United States Patent [19]
Williams et al.

[11] Patent Number: 5,387,194
[45] Date of Patent: Feb. 7, 1995

[54] REMOTE DISPLAY OF PATIENT MONITORED DATA

[75] Inventors: Eli Williams, North Salt Lake; Evan Call, Bountiful; Arlee Swensen, Layton, all of Utah

[73] Assignee: Surgical Technologies, Inc., Salt Lake City, Utah

[21] Appl. No.: 974,404

[22] Filed: Nov. 12, 1992

Related U.S. Application Data

[63] Continuation-in-part of Ser. No. 791,475, Nov. 12, 1991, Pat. No. 5,215,523, and Ser. No. 866,835, Apr. 10, 1992, abandoned.

[51] Int. Cl.⁶ .......................................... A61M 29/00
[52] U.S. Cl. ...................... 604/97; 128/904; 604/121
[58] Field of Search ............... 604/96–100, 604/65–67, 118, 121; 128/633, 709–712, 903, 904

[56] References Cited

U.S. PATENT DOCUMENTS

4,974,607  12/1990  Miwa .................... 128/904

Primary Examiner—John D. Yasko
Assistant Examiner—Adam J. Cermak
Attorney, Agent, or Firm—Trask, Britt & Rossa

[57] ABSTRACT

Apparatus for remotely displaying the inflation pressure within an inflator for inflating a balloon catheter. The apparatus comprises a pressure transducer positioned to sense pressure within the syringe, a transmission unit receiving a pressure signal from the transducer and transmitting by means of infrared light pulse sequences, a pressure message reflective of the pressure signal. A monitor positionable at a distance from the transmission unit receives and decodes the pressure messages, and provides a display thereof. A timer key for initiating the transmission of start/stop clock messages is located on the inflator unit. The monitor further includes a timer responsive to received clock messages, and an elapsed time display.

13 Claims, 7 Drawing Sheets

REMOTE DISPLAY OF PATIENT MONITORED DATA

RELATED APPLICATIONS

This application is a continuation-in-part of application Ser. No. 07/791,475 filed Nov. 12, 1991, now U.S. Pat. No. 5,215,523, and application Ser. No. 07/866,835 filed Apr. 10, 1992 (now abandoned).

BACKGROUND OF THE INVENTION

1. Field

The invention relates to medical monitoring technology and more particularly to a monitor for a device used in angioplasty.

2. State of the Art

Balloon angioplasty, technically referred to as percutaneous transluminal angioplasty, is a procedure performed by a cardiologist on a patient under local anesthesia to open arteries blocked with plaque or other fatty deposits. A catheter with a dilatable (inflatable or deflatable) balloon at or near its tip is threaded into and through an artery and to the stenotic region. The balloon is then inflated thereby compressing the plaque against and into the arterial wall. In this manner the vessel's interior diameter is widened to again permit sufficient flow of blood. This procedure is utilized in the peripheral arteries as well as the coronary arteries. A balloon catheter is described and illustrated in U.S. Pat. No. 4,519,403.

Typically, the balloon is inflated utilizing a fluid such as a mixture of equal parts of a contrast media and saline solution, which fluid exerts the dilation pressure. An inflation syringe assembly or device is utilized to deliver the inflation medium or fluid to the balloon as well as to provide the pressure needed for dilation. Continuous pressure readings can be obtained by having the inflation syringe assembly coupled in series to a pressure reading device such as a manometer.

It is important that the inflation syringe assembly not only deliver fluid and maintain the pressure but also, in particular, release the pressure rapidly when needed.

Typical quick-release syringe devices heretofore disclosed in the art include those described in U.S. Pat. Nos. 4,832,692 to Box et al., and 4,723,939 to Goodin et al. The Box device utilizes an external lever located above the syringe barrel to release a splined block which engages/disengages a threaded plunger rod. The Goodin device employs a threaded plunger rod which is engaged/disengaged by a rotatable locking knob. Actuation of these release mechanisms may require a change of hand position on the syringe assembly.

Additionally, for safe and effective operation of the inflation syringe, it is important that the user have knowledge of the pressure exerted by the inflation syringe and the time elapsed with the balloon in the inflated state. Thus, a pressure sensor is associated with a monitoring readout device which displays the pressure readings. Previous such readout devices have generally taken the form of a box-like device attached to the pressure sensor by a data communication cable, the box to be placed for the user's viewing. If the cable is short, the box adds clutter to the operating area adjacent the patient. Alternatively, if the cable is long so that the device may be placed away from the immediate operating area, the cable between the readout device and the syringe is cumbersome and may obstruct movement of medical personnel in the area proximal to the patient.

Additionally, many such monitors do not include a timer for keeping track of time elapsed during balloon inflation. The user must refer to a separate timekeeping device such as a watch, stopwatch or clock to keep track of elapsed time. Looking back and forth between the timekeeping device and the pressure display is inconvenient and may slow the user's reaction time in operating the syringe.

A need exists for a readout device for an angioplastic balloon catheter which can be remotely placed for viewing and provides a wireless transmission of data signals. A need further remains for such a monitor which includes a timekeeping display in a field of view adjacent to the pressure display.

SUMMARY OF THE INVENTION

A syringe assembly for inflating/deflating a balloon catheter has been invented which includes apparatus for remotely displaying the inflation pressure within the syringe. The apparatus comprises a pressure transducer positioned to sense pressure within the syringe, a transmission unit connected to receive a pressure signal from the transducer and operable to wirelessly transmit a pressure message reflective of the pressure signal, and a monitor positionable at a distance from the transmission unit. The monitor includes reception means for receiving the pressure message, and a display for displaying a pressure value communicated in the pressure message.

In the illustrated embodiments, the transmission unit includes an infrared light (I/R) transmitter and the pressure message is transmitted in the form of I/R pulses, especially digitized pulses. The transmission unit further includes a controller connected to the I/R transmitter, and operable to control the transmission of pressure messages. A timer key is also associated with the transmission unit for operation by a user to send clock messages to stop or start a timer which is located in the remote display unit.

The pressure signal produced by the transducer is an analog signal. Therefore, the transmission unit further includes an A/D (analog to digital) converter for converting the analog signal to a digital signal prior to transmitting the digital signal as a pressure or clock message.

The remote display unit further includes at least one microcontroller for decoding the received pressure and clock messages. The display unit microcontroller is constructed to verify the accuracy of each biphase data bit within a message and to require reception of two matching messages within a specified time frame before updating the display. The remote display unit also includes a timer and an elapsed time display. The timer is operable by means of start clock and stop clock Signals initiated by pressing the timer key on the inflator unit, to time an interval.

DETAILED DESCRIPTION OF THE ILLUSTRATED EMBODIMENTS

Figure 1:
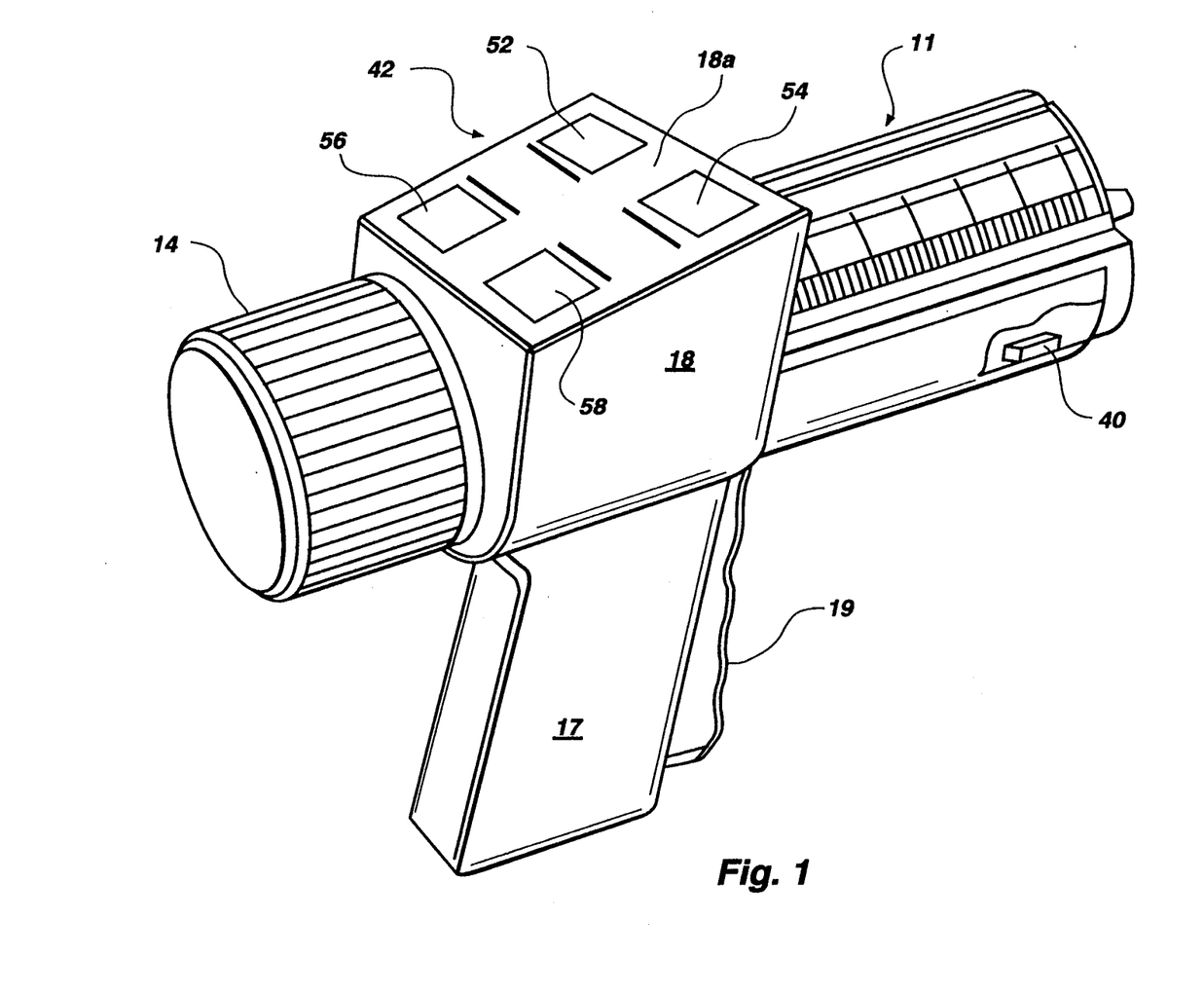
FIG. 1 is an external perspective view of a balloon catheter inflation syringe of the instant invention.

An external perspective view of the syringe assembly of the instant invention is presented in FIG. 1. The syringe body 18 of the syringe has a barrel 11 attached at its forward end. A knurled or ribbed knob 14 projects from the rear of the syringe body. Knurled knob 14 is connected to a threaded rod (not shown) at the rod's proximal end. The distal end of the rod is attached to a plunger.

Desirably, a pressure transducer 40 is disposed for reading the pressure within the syringe barrel (FIG. 1). Typically, transducer 40 produces an analog voltage output proportional to the applied pressure, which constitutes a pressure signal. Pressure transducer 40 is associated with an amplifier (not shown) for amplifying the pressure signal. The amplified pressure signal is then sent to a display unit indicated generally at 42 in FIG. 1.

In the embodiment of FIG. 1, display unit 42 includes panels 52, 54, 56, and 58 located on the top surface 18a of the syringe body 18. These display panels display operating information, such as the fluid pressure within the barrel sensed by transducer 40, elapsed time from a particular event, and the like.

As is apparent from the syringe assembly illustrated in FIG. 1, the instant invention provides a number of operational advantages over previous syringe assemblies. First, the operator of the syringe has a convenient, positive means, via the pistol-grip handle, of gripping (holding) the syringe assembly. The pistol-grip handle is shown in an opposite (polar) position to the display panels. However, the pistol-grip handle could be located from either side of the body 18, i.e., at 90° to the display panel. The bottom (polar) location, as shown in FIG. 1, is generally preferred since it can readily be operated effectively by either right- or left-handed operators.

The inflation syringe of the instant invention is particularly advantageous in being able to accommodate large volumes of inflation media, i.e., the device may have a barrel with large dimensions, either length or diameter or both. The barrel may have a greater diameter than typical syringes. For example, the displacement volume of the syringe plunger may be 30 cc or more. Thus, at a given pressure, e.g., 400 psi, there is more force on the large diameter plungers of the syringe of the instant invention than with conventional syringes. For example, the force on the plunger may be twice as great as for smaller plungers. This, of course, means that the disengagement force on the engagement/disengagement means must be significantly greater.

Figures 2, 2A:
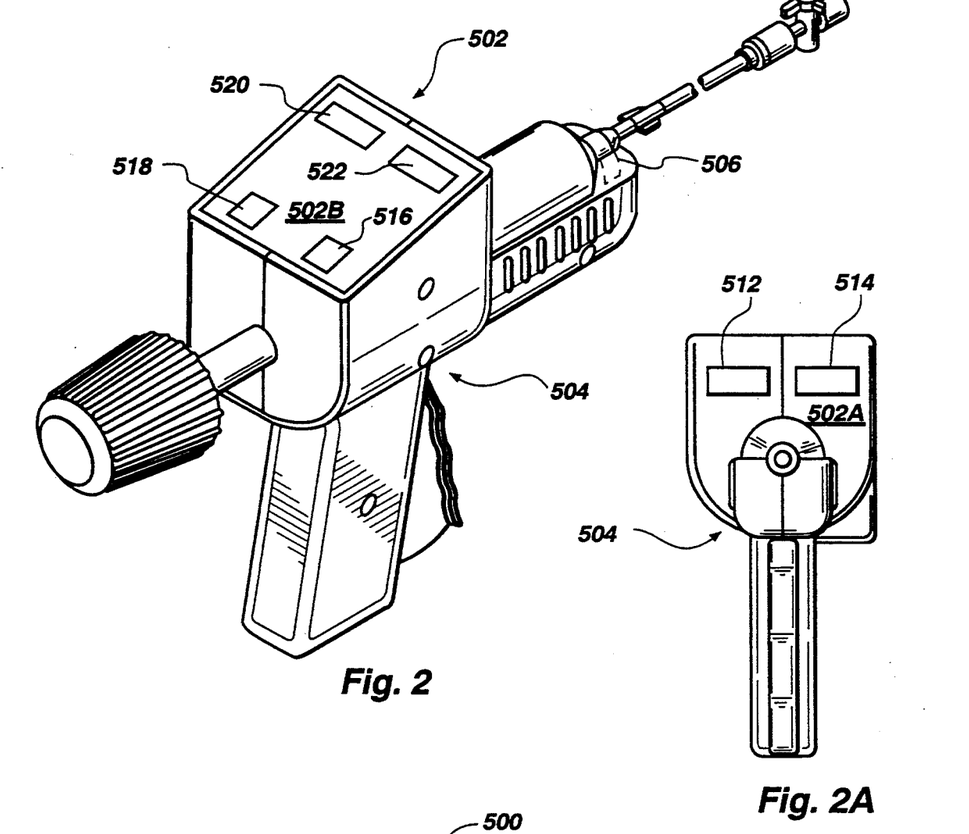
FIGS. 2 and 2A are respectively an external perspective view and a frontal view of an alternate embodiment of the inflation syringe.
Figure 2B:
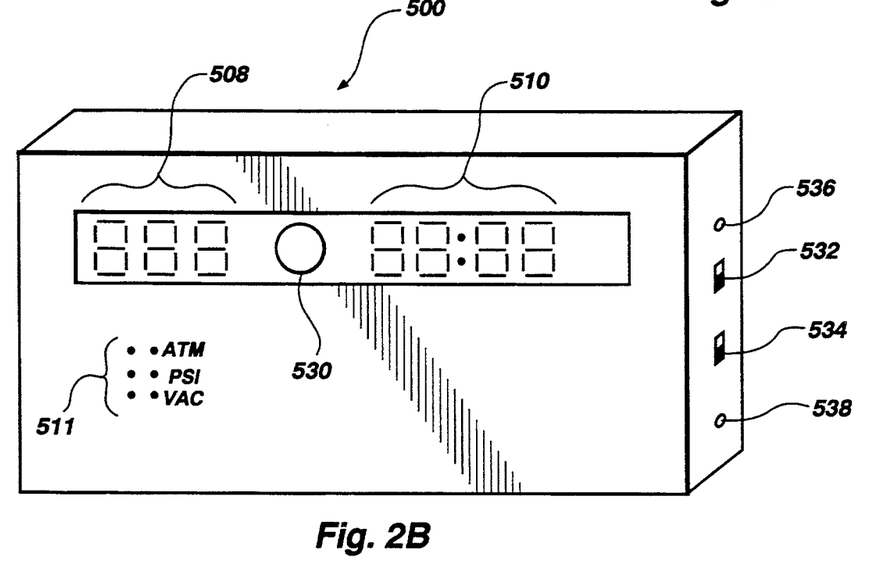
FIG. 2B is a perspective view of a remote display used in the alternate embodiment.

In an alternate embodiment, the display 42 with panels 52, 54, 56, 58 on the syringe body is deleted and replaced by a remote display unit 500 (FIG. 2B). Remote unit 500 can be positioned on a wall or the like for viewing by the user or other medical personnel. The handheld syringe unit 504 has a pressure transducer 506 positioned to sense pressure within the syringe near the end proximate the catheter attachment, and operably associated wireless transmission means 502. Wireless transmission means 502 is connected to receive and wirelessly transmit messages including pressure messages from transducer 506 to remote unit 500 which is positioned for convenient viewing by medical personnel. Remote unit 500 includes a pressure display 508 for displaying a pressure value reflective of the pressure sensed by transducer 506, and a time display 510 which indicates time elapsed from a user-designated start point.

Figure 5:
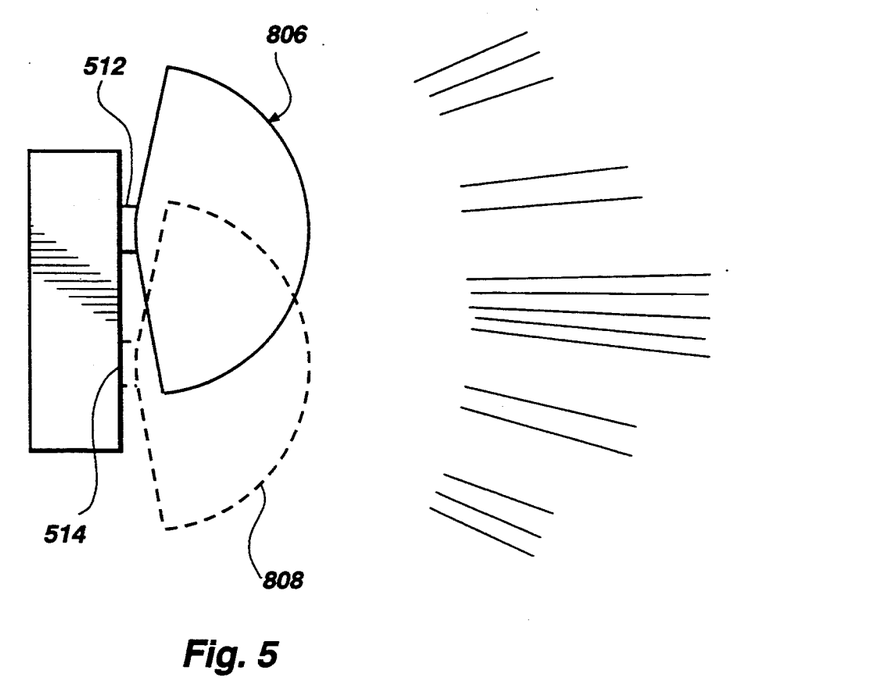
FIG. 5 is a diagram illustrating the overlap of transmission signals of a two-LED transmitter.

Transmission means 502 includes I/R pulse means for sending digitally-coded I/R pulse sequences. The I/R pulse sequences include clock messages reflective of the start or finish of a time interval, or pressure messages communicative of the pressure sensed by transducer 506. In the illustrated embodiment, the I/R pulse means comprises two I/R LEDs 512, 514 disposed on the front surface 502A of transmission unit 502 (FIG. 5A). LEDs 512, 514 simultaneously transmit identical I/R pulse sequences. Optionally and desirably, LEDs 512, 514 are covered by a lens (not shown) which does not interfere with transmission of I/R pulses but which protects against contamination of the electronic components with fluids.

In the illustrated embodiment, LEDs 512, 514 each transmit an infrared signal subtending a transmission arc of about 165°. LEDs 512, 514 are arranged to have their respective transmission arcs 806, 808, overlapping, preferably about 100° (FIG. 5). This arrangement provides a strong signal in the central overlap region with a minimum of parts, for more accurate and reproducible transmission. Alternatively, LEDs 512, 514 could be replaced by a single LED or by three or more LEDs. In another embodiment, one or more infrared laser diodes could replace the LED(s) as the infrared light transmitter.

Power key 516 is a momentary-type key for turning transmission means 502 on and off. Time key 518 is a momentary-type key for a user to press to designate the start or end of a time interval. In response to pressing of time key 516, transmission means 502 sends a clock message via I/R LEDs 512, 514. Transmission means 502 also has indicators 520, 522. Indicator 520 is turned on steady when the unit is on, and flashes when time key 518 is pressed to start a time interval. Indicator 522 is turned on when the handheld unit is initialized in an invalid condition, based upon the pressure sensed by transducer 506 when power key 516 is pressed to turn transmission means 502 on.

Remote display unit 500 includes a detector window 530 for detecting the I/R pulse sequences, and a display 510 for displaying pressure values communicated in the transmitted digital signals. A set of indicators 511 indicates whether the pressure reading shown in pressure display 510 is in units of atmospheres, psi, or inches of mercury (the latter is only displayed if there is a below-atmospheric pressure in the syringe). Remote unit 500 also includes a time display 520 for displaying the time elapsed from a start point designated by a user pressing time key 516. Remote unit 500 further includes on/off switch 532 and units switch button 534 (both two-position switches); and jacks 536, 538. Jack 536 is a power jack for receiving an external power input, while jack 538 is for a chart recorder output.

In a further embodiment of the transmitter and remote display (not illustrated), the transmitting LEDs 512, 514 are positioned on the top surface 502B of the transmission means 502, instead of on the front surface 502A. The receiver portion of remote unit 500 is then positioned above the user, for example on the ceiling. The display portion is mounted for viewing on a wall or similar convenient viewing location, and is electrically connected by a cable to the receiver portion to receive the display signals. Receiver unit 500 may, alternatively, be a receiver/transmitter which receives IR signals from a transmitter and then re-transmits them to a remote receiver/display thus obviating the need for any cable connections.

The embodiment of the preceding paragraph offers some further advantages in that it is much easier for a user to keep the infrared transmitters aimed towards the remote receiver. The user has greater freedom of movement and the necessity for particular positioning of the patient and/or the user holding the transmitter syringe, so that the front 502A is aimed generally toward the remote receiver, is avoided. The associated cable of this embodiment is positioned on the ceiling and extends down from the upper edge of walls or the like, so it will not be an obstacle to personnel moving about the area.

Figure 3:
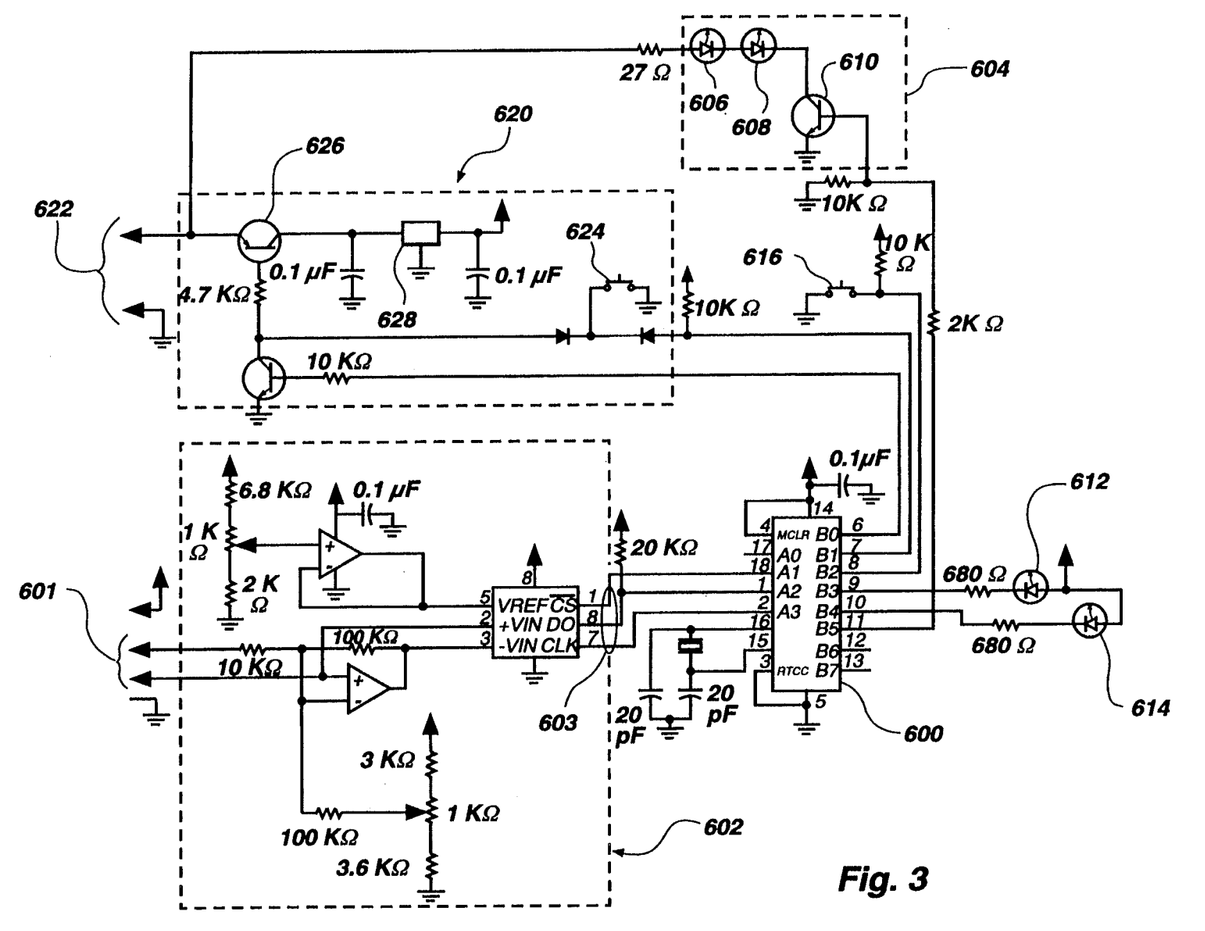
FIG. 3 is a circuit diagram of a transmission means of the readout apparatus.

FIG. 3 depicts circuitry for a working embodiment of transmission means which may be incorporated into syringe body 18. A microcontroller 600 comprises a central processing unit (CPU), read only memory (ROM) random access memory (RAM), timer unit and watchdog timer. Micro-controller 600 is here selected to be a microchip 16C54, Microchip Technology Corp. is the supplier of this microchip and the other microchips identified herein having a ROM of the OTP (one-time programmable) type. However, a chip with an EEPROM or EPROM could also be used. In the illustrated embodiment, the OTP ROM is programmed with the appropriate software prior to installation in the circuit board. Microcontroller 600 is constructed to perform or control all major functions associated with syringe 10, including all required timing functions, generation of the IR transmission, managing of the power control circuit, and the reading and averaging of pressure signals received from transducer 506.

Transducer 506 provides pressure signals, which are electrical signals proportional to sensed pressures, at inputs 601 which is connected to an analog-to-digital (A/D) converter 602 for converting the analog pressure signal to a digital signal communicative of the sensed pressure. This is because a digitally coded signal is preferred for wireless transmission, whereas a typical pressure transducer outputs an analog electrical signal. A/D converter 602 is in turn connected to microcontroller 600 at outputs 603.

In a preferred embodiment, microcontroller 600 takes readings at 100 millisecond intervals, or in other words, ten times a second. Further preferably, micro-controller 600 computes a computed pressure reading which is obtained by averaging two current readings, then taking the result and averaging it with the previously computed pressure reading. The new computed pressure reading thus obtained is sent to an infrared transmitter 604 for transmission as infrared light pulses to the receiving unit. Averaging the pressure readings in such a fashion smooths out noise.

Microcontroller 600 is further constructed to vary the rate of message transmission according to the stability of the pressure signal received from transducer 506. The pressure signal is sampled about every 100 milliseconds. If the pressure changes by 2 psi or less, messages are sent at one-second intervals. If the pressure changes by more than 2 psi, pressure messages are sent five times per second. By so varying the transmission rate, drain on the battery is reduced and the accuracy of transmission is increased. The maximum display update rate is thus 5 times a second. Such an update rate allows pressure changes to be rapidly reflected in the display, yet holds individual values long enough that they can be easily read by a viewer.

Infrared transmitter 604 comprises two infrared LEDs 606, 608 (equivalent to 512, 514 in FIG. 5) in series with a transistor 610 which functions as a power switch. Transistor 610 is connected to microcontroller 600 to be controlled in an on/off fashion.

Indicators 520, 522 of FIG. 5 are here embodied as LEDs 612, 614, which are connected to be operated by microcontroller 600 to indicate power on/timing and invalid setup, respectively. LED 612 is responsive to switch 616 which is a momentary switch activated by pressing of time key 518. When time key 518 is pressed, an I/R clock message is sent . by transmitter 604. If the previous clock message was a stop clock message, the instant message is a start clock message, and vice-versa. Upon initiation of a start clock message, the timing LED 612 is flashed. Otherwise, timing LED 612 is steadily on as long as the unit is turned on.

Power management functions are effected through power control circuitry indicated generally at 620. In the working embodiment, power is received at inputs 622 from a 9 volt battery which is installed in the hand-held syringe unit. An on/off switch 624 governs the supply of power to microcontroller 600. When switch 624 is turned "on" a transistor switch 626 is activated to send power to a voltage regulator 628. Voltage regulator 628 outputs +5 volts which powers microcontroller 600 and A/D converter 602. IR LEDs 606, 608 of transmitter 604 are connected to receive +9 volts directly from inputs 622.

Microcontroller 600 is further desirably constructed to perform an initialization routine. The initialization routine begins when power is first supplied to the transmission means. Lighting of power LED 612, which is connected to microcontroller 600, indicates that power is on. Next, the current pressure sensed by transducer 506 is read, and if it is more than 10 psi below atmospheric pressure, or more than 25 psi above atmospheric, an invalid setup LED 614 is lit. The power is automatically cut off via transistor switch 626 two (2) seconds after the on/off switch 624 is released. If the pressure sensed is within the above-cited lower and upper limits, the current pressure reading is used as a zero offset value for the current session.

Figure 4:
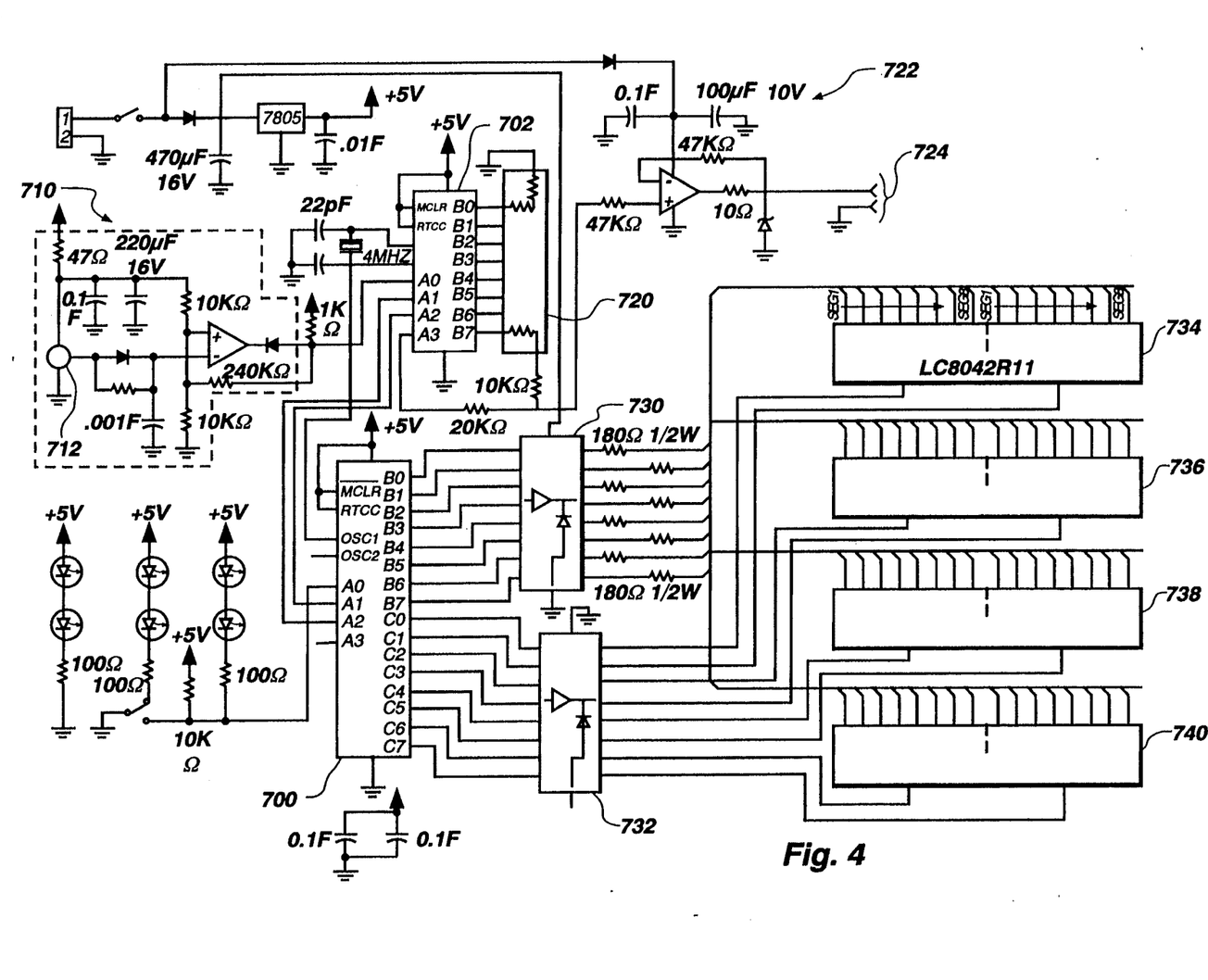
FIG. 4 is a circuit diagram of a remote receiver/display unit of the readout apparatus.

Turning to FIG. 4, circuitry for a working embodiment of the remote display unit 500 will be described. Remote unit 500 has two microcontrollers 700, 702. This is because of the time critical nature of the two tasks of the remote unit: reception of the wireless transmission and display multiplexing.

Microcontroller 702 handles the timing and data verification required for receiving the I/R transmissions sent from transmitter 604 on syringe 10. Microcontroller 702 decodes the transmitted digital pressure signals and converts the value of pressure communicated by the transmitted signals from psi to atmospheres. In the working embodiment, microcontroller 702 is selected to be a 16C54, the same chip as used in the transmission unit. Microcontroller 702 is connected to receive filtered signals reflective of the transmitted pressure signals from I/R receiver generally indicated at 710. I/R receiver 710 comprises a hybrid I/R receiver 712 having built-in automatic gain control, with operably associated bandpass filtering.

Optionally, in order to provide an electrical signal output reflective of the pressure signals for a chart recorder, an R2R resistor, from the Bourns Co., network chip 720 is connected to microcontroller 702 to function as a digital-to-analog (D/A) converter. Chip 720 is in turn connected to scaling and protection circuits indicated generally at 722, which output the analog pressure signal at jacks 724. A chart recorder may be connected to receive the analog pressure signals at jacks 724.

Microcontroller 702 is constructed to decode the received pressure and clock messages as follows. In the working embodiment, both pressure and clock messages are transmitted in the form of biphase data bits each having first and second portions. Transmitter controller 600 generates the biphase bits such that if the first portion is high, the second portion is low, and vice-versa. During the time required for transmission of one portion of the biphase bit (about 500 microseconds), the received signal is sampled many times. Microcontroller 702 then determines, based on a majority of the samples, as to whether the immediately received portion of the biphase bit is high or low. If a bit is received in which both the first and second portions are high, or both are low, the message is discarded. This system of requiring that each biphase bit include both a high and a low portion, helps to eliminate erroneous messages caused by noise and stray infrared signals picked up by the detector 530.

Microcontroller 702 is further constructed to wait for two transmitted messages to match exactly before considering the message valid and sending a message signal to display controller 700. Transmission means 502 is constructed to send three copies of each message per pressure reading, so that one may be lost without loss of the message. Each pressure message comprises nine biphase bits, while each clock message comprises six biphase bits. The difference in length of the two types of messages allows microcontroller 702 to distinguish between them.

In the illustrated embodiment, pressure messages are communicative of the pressure reading in PSI. If a user desires, the pressure value may be displayed in atmospheres by operation of the Units switch 534 on the display unit. If atmospheres are selected, microcontroller 702 makes a conversion from PSI to atmospheres. Should the pressure go negative, a conversion from PSI to inches of mercury (inHg) is done by display microcontroller 702. Negative pressure is always displayed as inHg.

Microcontroller 700 is constructed to operate the seven segment display. In the working embodiment, microcontroller 700 is selected to be a MICROCHIP 16C55, which is functionally identical to the 16C54 except that it has more input/output pins. A high-side driver 730 (chip UDN2981) and a low-side driver 732 (chip ULN2804) are connected to receive multiplexing LED control signals from microcontroller 700. Drivers 730, 732 are in turn connected to drive LED segments 734, 736, 738, 740 which each comprise two seven segment LED displays. Drivers 730, 730 are required because microcontroller 700 does not have sufficient drive capability to drive LED segments 734, 736, 738, 740.

Microcontroller 700 controls the output of drivers 730, 732 to provide binary-to-seven segment conversion of the data and display multiplexing of LED segments 734, 736, 738, 740. The seven-segment LED displays are multiplexed at a ⅛ duty 125 Hz rate. Multiplexing is used to provide a low parts count hardware design. LED segments 734, 736, 738, 740 are identical and are here selected to be LC8042R11 chips.

Microcontroller 700 is further operable to perform time-keeping functions. A clock message received by microcontroller 702 (the receiver microcontroller) is sent directly to microcontroller 700 (the display microcontroller). When a clock message signalling the start of a time interval is received, the display controller increments the time display by one second every second to a maximum value of 99 minutes 59 seconds. When a clock stop or clock reset message is received, the time display is not incremented. If a clock reset message is received, the clock counters are reset to zero. If no messages are received during any 3 second interval, microcontroller 700 flashes all seven (7) segment displays at a 1 Hz rate to inform the user of an interruption in I/R communications.

Microcontrollers 700, 702 are mutually interconnected and adapted to provide for the exchange of information between them. Accordingly, both microcontrollers 700, 702 are constructed to perform an efficient, two wire, bi-directional, serial communication routine.

The wireless transmission unit provides several advantages for medical personnel. The display can be positioned so that the user of the syringe unit can quickly look from the remote unit to other displays such as EKG, etc, which are nearby. No wires are needed to communicate the data to the display, so no extra wires are added to become obstacles to other medical personnel moving in the area. The provision of a timer easily operated on the handheld unit, with an elapsed time display adjacent the pressure display on the remote unit, is a great convenience for a user. Many users formerly used a watch or room clock to time inflation/deflation procedures, or had a technician keep time and call it out, the latter method further adding to confusion and noise in the operating area.

A wireless transmitter in conjunction with a remote receiver/display unit may provide advantages for other types of surgical/medical instruments and procedures besides angioplasty. The system could be adapted to any handheld device which can include a sensor positioned to sense a critical operating condition of the device or an organic condition of the patient's tissues near the device, or when precise timing of procedures with the handheld unit is needed. Such a sensor should be adapted to produce an electrical signal reflective of the condition being sensed.

The invention, for example, is readily adaptable to monitor blood pressure, pulmonary artery pressure, central venous pressure, left atrial pressure, saturation of arterial oxygen, saturation of venous oxygen, temperature and similar physiological data.

Figure 6:
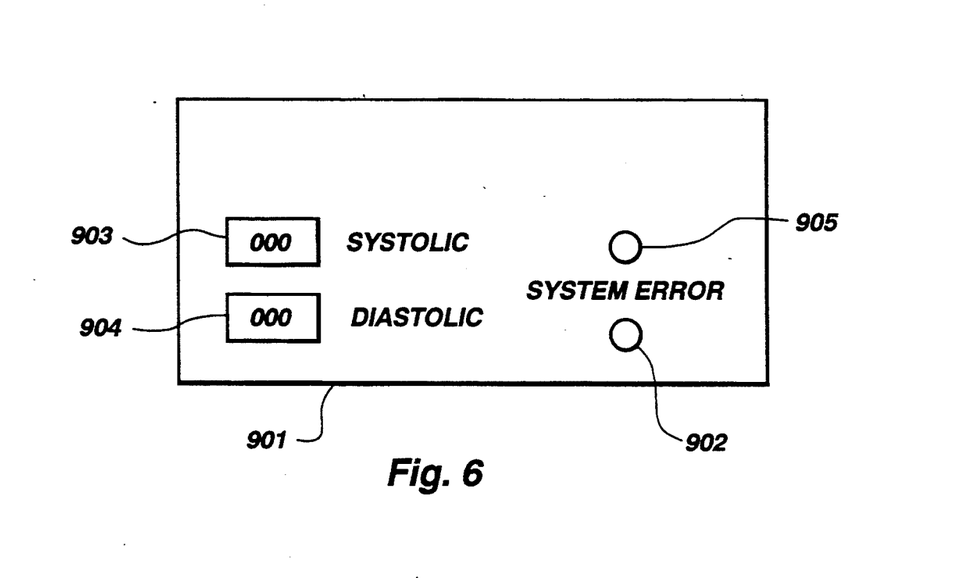
FIG. 6 is an elevational view of a remote infrared blood pressure monitor display.

A remote blood pressure monitor display is illustrated in FIG. 6. The monitor display 901 contains an infrared receiver 902 which receives data via infrared data signals emitted from an infrared transmitter (see FIG. 7). The blood pressure is numerically displayed in windows 903 and 904, which show systolic and diastolic pressure, respectively. Windows 903 and 904 may contain liquid crystal displays or LED displays.

In the event an error signal is detected, the system error light 905 is illuminated to indicate an error signal exists. The electronic mechanism for interpreting the coded LED signal received by the remote display, converting the coded signal to a display signal and internally transmitting the display signal to window 903 or 904, is similar to the electronic mechanism utilized for the remote display illustrated in FIG. 2B and FIG. 4.

The blood pressure of a patient is monitored by inserting a catheter (not shown) into an artery. The catheter communicates with tubing 906 which permits arterial blood to come into contact with a blood pressure transducer (not shown) which detects the systolic and diastolic pressures within the artery. For a very accurate determination, the catheter may be placed adjacent the heart near the left ventricle. The transducer is located in a transducer base. The transducer converts the detected pressure to an electrical signal, typically an induced voltage which is proportional to the pressure applied to the transducer. Transducers of this type are readily available in the art.

The transducer base contains an internal cavity which communicates with tubing 906. A portion of the cavity wall is formed by the transducer. Thus, blood from the patient is in contact with the transducer. The transducer base 907 is preferably disposable so that no cross-contamination of blood from one patient to another can occur.

Figure 7:
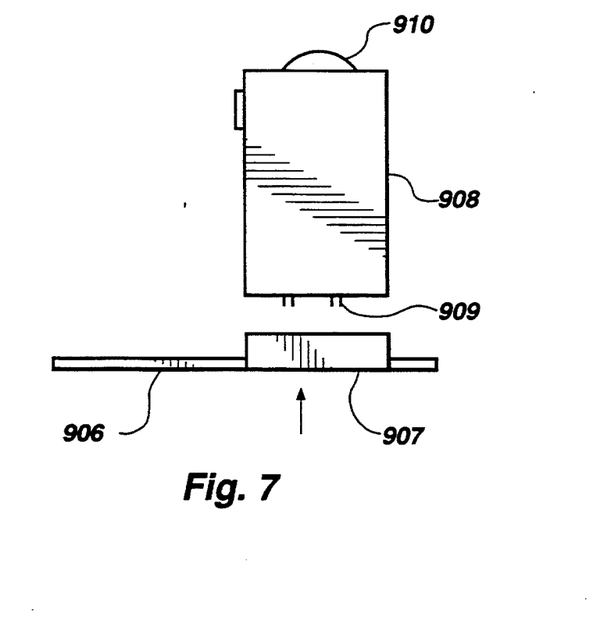
FIG. 7 is an elevational view of an infrared LED blood pressure transmitter.

The LED data transmitter 908 plugs into the transducer base 907 via connection pins 909. The voltage generated by the transducer is conveyed via connector pins 909 to the LED data transmitting device. The voltage is processed in the transmitter 908 in a manner similar to that illustrated by FIG. 6 wherein the analog voltage signal is converted to a digital signal before being transmitted by one or more infrared LEDs 910 to the remote display.

In connection with the infrared LED data transmitter or with the remote monitor display may be included an annunciator circuit which audibly announces the displayed information. A similar system to that described for blood pressure monitoring may be used to detect and monitor pulmonary artery pressure, central venous pressure, left atrial pressure, saturation of arterial oxygen, saturation of venous oxygen, temperature or the like by the use of an appropriate sensor.

The wireless transmitter in association with a pressure transducer, combined with the remote monitor, could also be adapted to any inflation device structured for pressurizing an inflatable vessel, not necessarily for a medical device.

Various advantages are provided by the wireless line-of-sight transmitter/remote receiver system. The low power light or sonic signal is simple and accurate for relatively short-range, line-of-sight transmission, and will not interfere with other electrical signals in nearby medical monitors and equipment. The handheld unit (e.g. the unit of FIG. 5) is completely self-contained including power source, and thus does not entail wires or cables which obstruct movement of the user or of medical personnel in the crowded surgical area. Also, the wireless transmitter consumes a relatively small amount of power.

The instant invention employs line-of-sight transmission from a transmitter to a remote receiver to transmit patient data for remote, centralized display. Infra-red signals are a preferred manner of data transmission although other line-of-sight signals are useful such as ultra-sound and laser beams. Laser beams particularly useful are those which are refracted or diffused to cover a broad field.

An ultrasound transmitter utilizes a transponder to emit ultra high frequency sonic vibrations. The frequency is sufficiently high that it is well above the human reception range. Also, because of such a high frequency, there is virtually no interference from human voices and other sounds in an operating room. Information can be conveyed by impulses or by changes in frequency.

Line-of-sight (LOS) transmission means is especially desirable for the purposes of the instant invention inasmuch as it does not interfere with other types of transmission, e.g. RF signals, nor are LOS transmissions interfered with by other types of signals such as RF signals. Given the need for extreme accuracy of the displayed information during operation, e.g. TLAP procedures, non-interference by other signals is very important. Furthermore, LOS transmissions are confined to a particular room so that governmental agency, such as FCC, approval is not required.

Generally, the transmitter of the instant invention is part of a handheld device. The range of transmission need not be great, e.g. generally less than 50 feet. The field, however, should be very broad so that the transmitter need not be aimed directly at the receiver. If sufficient power is applied to an IR, ultrasound or laser transmitter, the signals may bounce off room surfaces to be received accurately by the remote receiver.

In many instances, the remote receiver may be located in an overhead location in close proximity, e.g. less than 15 feet, to the hand-held transmitter so that there is little likelihood of interference by other objects and a low-powered transmitter can be utilized. Since the transmitter is often a TLAP catheter and connected to a patient, it is very desirable that it not be tethered to other objects, such as AC power sources. Thus, the transmitter is preferably battery powered.

The remote transmission/monitoring aspect of the instant invention is applicable to non-invasive procedures as well as to invasive procedures.

Patients being monitored during stress tests, for example, have various functions such as blood pressure, pulse rate, respiration rate, temperature, blood oxygen content and the like being monitored. Because a stress test requires physical activity, i.e. exercise, on the part of a patient, it is awkward and inconvenient to have the patient tethered by various wires to monitoring devices.

Because of the small, compact construction of the transmitting device of the instant invention, the transmitter may be directly attached to a patient so that, if necessary, the patient could be entirely mobile, to move freely while exercising and even to move from one exercise apparatus to another or from one test station to another.

Figure 8:
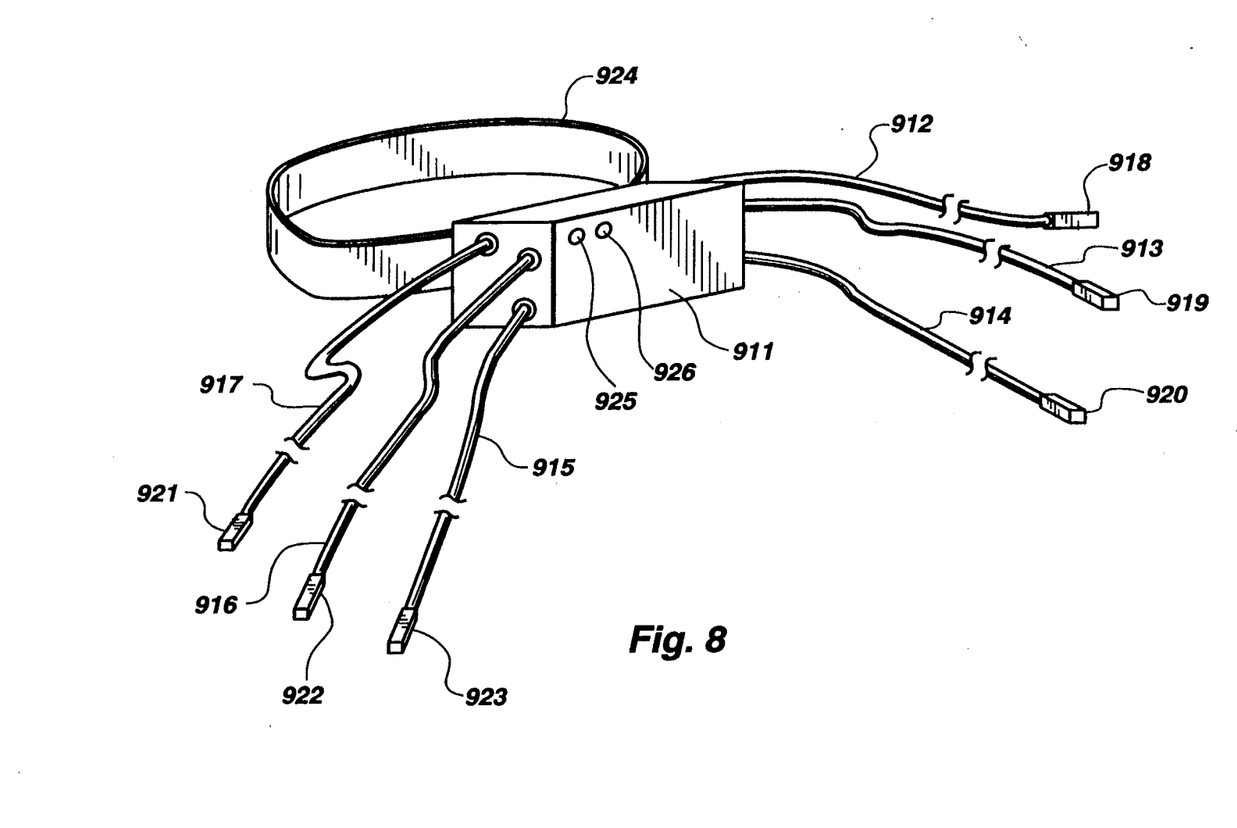
FIG. 8 is a perspective view of an IR transmitter supported by a patient-attachment device.

A transmitter suitable for direct attachment to a patient, exerciser, or other person being monitored for various physical characteristics is illustrated in FIG. 8. The transmitter can transmit a multitude of physical characteristics such as pulse rate, temperature, blood oxygen level, respiration rate, metabolism rate ($CO_2$ content in exhaled gases), blood pressure and the like. These characteristics may be detected by thermocouples, transducers, transponders and like sensors.

An oximeter suitable for attachment to a finger nail, ear or other sensitive area may be used to detect blood oxygen level. A thermocouple may be used to detect body temperature while transducers may be utilized to detect blood pressure, either with or without an inflated pressure cuff. Either a transducer or transponder (stethoscope type device) can be used to detect pulse rate. All of these devices, which are well known in the art, are capable of emitting a detectable signal which has a relationship to the characteristic being detected. A stethoscope device emits a sonic signal which may be converted to a corresponding electrical signal while the other devices generate directly an electrical signal.

These electrical signals are communicated to the transmitter which "reads" each signal sequentially and transmits it via light or sound means to a remote monitor/display. The transmitter described herein has the ability to read signals at the rate of about 20 signals per second. Thus, if five characteristics were being monitored, consecutive readings for a particular signal would be read four times per second, which is a rate of 240 times per minute. The transmitter may, however, be modified to read signals at a faster rate to provide more frequent consecutive readings for a particular characteristic being monitored.

The transmitter has light or sound transmitting means to transmit line-of-sight signals within a certain locality, e.g., within a health care facility. Such IR transmitting means, described hereinabove, has a wide-angle transmission area so that movement of the person to whom the transmitter is attached does not unduly interfere with signal transmission. A multi-signal (multi-characteristics) transmitter has encoding means which provides each distinct signal with an identifying prefix so that an individual signal for a given characteristic is identified properly by the remote receive and display. The remote display may have a single display window with a visual identification of the particular characteristic being displayed. Also, optionally, an annunciator may be incorporated in the display to announce the particular characteristic being displayed. The characteristic itself may also be announced.

A separate display window for each characteristic to be displayed is generally preferable. The remote receiver/display unit has a plurality of windows so that all the characteristics being monitored may be viewed in a single glance. A single receiver/display unit preferably with multiple display windows may be utilized to monitor a plurality of transmitting units, if desired.

The device illustrated in FIG. 8 is a signal processor/transmitter similar in construction and function to that described and illustrated with reference to FIGS. 2, 2A and 3. The signal processor/transmitter 911 has a plurality of lead wires 912, 913, 914, 915, 916 and 917 attached to it. The lead wires contain various sensing elements 918, 919, 920, 921, 922 and 923 at their distal ends.

The various sensors may include a temperature sensor, e.g. a thermocouple type device, a pressure transducer to sense blood pressure, a sonic sensor to sense pulse or respiration rate.

Electrical signals from the sensors 918–923 are transmitted by the lead wires 912–917 to the signal processor/transmitter wherein the signals are processed, i.e. encoded with an appropriate prefix and converted into a numeric signal for transmission by RF means or IR means, such as the broad beam IR transmitters 925 and 926 for receipt by a remote receiver/display device. A head band 924 is structured to hold signal processor/transmitter 911 in position on a person's head. The lead wires 912–917 can then depend to various parts of the body, spider-fashion, without interfering with one another or unduly with the person to whom they are attached. Also resting the transmitter on the head of a person being tested is a good location for line-of-sight transmission of IR signals, for example, tests on treadmills and the like usually are done with a person's head erect and with very few arm motions above the head.

The signals are received, processed and displayed by a receiver/display device similar to that illustrated and described with reference to FIGS. 2B and 4.

The transmitter may also be supported on a patient by means of a chest harness. This means of support may be desirable for use with patients who tend to put their head down during exercise. Using dual IR emitter such as illustrated is FIG. 5 increases the zone of effective transmission. Such dual emitters may be arranged vertically or horizontally to provide the widest possible band of transmission. Strong IR signals will reflect from the hard surfaces (walls, ceilings, etc.) found in most stress test facilities. Thus, with wide band transmissions and reflection, the IR signals are generally received by the receiver regardless of the orientation of the transmitter.

Thus, for the purposes of this invention, line-of-sight transmission defines light and sound transmissions, generally of low power, and does not include RF generated signals. Even low power RF transmitters, e.g. garage door openers, readily penetrate walls, structures, etc.

The invention has been described in detail with regard to IR signals being utilized to carry a data message signal from a transmitter to a remote receiver display, including the use of an intermediate transceiver (receiver/transmitter) which re-transmits the IR data signal. Preferably the transceiver incorporates an IR receiver similar to that described hereinabove with reference to the receiver/display unit and an IR transmitter similar to that described with reference to the primary IR transmitter.

Sonic data signals may be transmitted by substituting a transponder for the IR transmitter and a receiver transponder for the IR receiver. The transmitting and receiving transponder may be similar structurally. The transmitting transponder has a sensor signal receiving means which had an A/D converter similar to the IR transmitter and means for electrically stimulating a diaphragm in correlation to said sensor signal to emit a sonic data signal correlative to said sensor signal. The transponder receiver has a diaphragm which receives said sonic data signal and generates an electrical signal correlative to said sonic data signal, said electrical signal being fed to said display unit to display data which correlates to a monitored condition of a patient. Other types of transponders may be utilized, for example, certain solid state devices such as piezoelectric devices generate sonic signals when electrically stimulated and vice versa.

Laser diodes could be substituted for the IR diodes to transmit a laser data signal.

While specific embodiments of the invention have been illustrated and described herein, the invention is not intended to be limited thereto, but is to include all the embodiments, variations and modifications encompassed within the appended claims.

What is claimed is:

1. Apparatus providing wireless transmission of a sensed parameter to a remote display unit, in combination with a medical device of the kind including a sensor for sensing a desired parameter, comprising:

a sensor operably associated with said medical device for sensing an operating condition of said medical device or a tissue condition of a patient to whom said medical device is affixed, and providing a sensor signal reflective of said condition;

transmitter means connected to said sensor to receive said sensor signal, and having means to wirelessly transmit a line-of-sight sensor message communicative of said condition, said transmission means including a wireless transmitter;

a power source connected to power said transmitter means; and a remote display device placeable at a distance from said transmitter means, connectable to a second power source to receive operating power, and including:

signal reception means for receiving said line-of-sight sensor message and providing a message display signal in response thereto, and message display means connected to said signal reception means for receiving said message display signal and providing a display reflective thereof.

2. The apparatus of claim 1, wherein said wireless transmitter is an infrared light transmitter, said sensor message comprises an infrared signal, and said remote display device includes infrared detection means for receiving said infrared signal sensor message and signal translation means connected to said infrared detection means for receiving and translating said infrared signal into a display signal indicative of thereof.

3. The apparatus of claim 2, wherein said infrared light transmitter comprises at least one infrared LED having a transmission arc through which said infrared LED effectively transmits said infrared signal.

4. The apparatus of claim 3, wherein said infrared light transmitter comprises a plurality of LEDs mutually positioned to have their said respective transmission arcs overlapping.

5. The apparatus of claim 3, wherein said infrared light transmitter comprises a pair of LEDs positioned to have said respective transmission arcs overlap by about 100°.

6. The apparatus of claim 2, wherein said infrared light transmitter comprises at least one infrared laser transmitter.

7. The apparatus of claim 1, wherein said sensor signal is an analog signal, and said transmission means further includes an A/D converter for converting said analog signal to a digital signal constituting said sensor message.

8. The apparatus of claim 7, wherein said transmitter unit further includes a controller connected to said A/D converter to receive said digital signal and having means to control the transmission of said sensor message.

9. The apparatus of claim 8, wherein said transmitter unit further includes a timer key connected to said controller, said controller having means to control said wireless transmitter to transmit a clock message in response to pressing of said timer key by a user.

10. The apparatus of claim 9, wherein said remote display unit further includes:

a time display, and a display controller connected to said time display and said receiving unit, said display controller having means to count time elapsed from receipt of a start clock message and means to provide time display signals reflective thereof to said time display.

11. The apparatus of claim 8, wherein said controller has means to compute said sensor message by averaging at least two successively received sensor signals to produce an averaged sensor signal.

12. The apparatus of claim 11, wherein said controller has means to compute said sensor message by averaging said averaged sensor signal with an immediately preceding averaged sensor signal, to produce a twice-averaged sensor signal.

13. Apparatus combining a remote display and an inflator for inflating a balloon catheter, comprising:

a pressure transducer having means to sense pressure within an inflator of a balloon catheter, and providing a pressure signal reflective thereof;

a transmission unit communicating with said inflator to receive said pressure signal from said pressure transducer, and having means to wirelessly transmit a pressure message in response thereto, said transmitter unit including a wireless transmitter;

a power source connected to power said transmitter unit; and a display device constructed to be positionable at a distance from said transmitter unit, connectable to a second power source to receive operating power, and having means to receive said pressure message and to provide a pressure display reflective thereof.

* * * * *

UNITED STATES PATENT AND TRADEMARK OFFICE
CERTIFICATE OF CORRECTION

PATENT NO. : 5,387,194
DATED : February 7, 1995
INVENTOR(S) : Williams et al.

It is certified that error appears in the above-indentified patent and that said Letters Patent is hereby corrected as shown below:

In col. 2, line 55, change "Signals" to --signals--;

In col. 5, line 32, insert a comma after "herein";

In col. 6, line 21, after "sent" delete the period;

In col. 6, line 33, insert a comma after "on";

In col. 8, line 8, change "LC8042R11" to --LC8042R-11--;

In col. 11, line 33, change "receive" to --receiver--.

Signed and Sealed this

Twenty-first Day of January, 1997

Attest:

BRUCE LEHMAN

*Attesting Officer*    Commissioner of Patents and Trademarks